(12) United States Patent
Kim et al.

(10) Patent No.: US 12,000,818 B2
(45) Date of Patent: Jun. 4, 2024

(54) DEVICE FOR WATER EXAMINATION

(71) Applicant: THE WAVE TALK, INC., Yuseong-gu Daejeon (KR)

(72) Inventors: Young-Dug Kim, Seongnam-si (KR); Kyuong man Cho, Seoul (KR); Guk hyun Nam, Seoul (KR)

(73) Assignee: THE WAVE TALK, INC., Yuseong-gu Daejeon (KR)

( * ) Notice: Subject to any disclaimer, the term of this patent is extended or adjusted under 35 U.S.C. 154(b) by 252 days.

(21) Appl. No.: 17/600,521

(22) PCT Filed: Sep. 24, 2020

(86) PCT No.: PCT/KR2020/012995
§ 371 (c)(1),
(2) Date: Sep. 30, 2021

(87) PCT Pub. No.: WO2022/059829
PCT Pub. Date: Mar. 24, 2022

(65) Prior Publication Data
US 2022/0317104 A1 Oct. 6, 2022

(30) Foreign Application Priority Data
Sep. 18, 2020 (KR) .......................... 10-2020-0120698

(51) Int. Cl.
*G01N 21/51* (2006.01)
*G01N 21/47* (2006.01)
(Continued)

(52) U.S. Cl.
CPC ......... *G01N 33/18* (2013.01); *G01N 21/4788* (2013.01); *G01N 21/51* (2013.01); *G01N 21/85* (2013.01); *G01N 2021/479* (2013.01)

(58) Field of Classification Search
CPC ........... G01N 21/47; G01N 2021/4733; G01N 2021/479; G01N 21/51
See application file for complete search history.

(56) References Cited

U.S. PATENT DOCUMENTS 10,852,246 B2 * 12/2020 Kim .................... G01N 21/4788
10,921,336 B2 * 2/2021 Hansen .................. G01N 35/04
(Continued)

FOREIGN PATENT DOCUMENTS

JP 2018-536856 A 12/2018
JP 2019058126 A 4/2019
(Continued)

OTHER PUBLICATIONS

International Search Report and Written Opinion for PCT/KR2020/012995 mailed Jun. 15, 2021, all pages.
(Continued)

*Primary Examiner* — Rebecca C Bryant
(74) *Attorney, Agent, or Firm* — Kilpatrick Townsend & Stockton LLP

(57) ABSTRACT

Provided is a water examination device including: a main body; a cup accommodation unit formed inward from a surface of the main body such that a cup containing a fluid is accommodated therein; a wave source for irradiating a wave toward the cup accommodation unit; a detector for detecting a laser speckle generated by multiple scattering of the irradiated wave in the fluid, at every time point set in advance; and a controller for estimating whether foreign substances exist in the fluid in real-time by using the detected laser speckle.

11 Claims, 12 Drawing Sheets

(51) Int. Cl.
    *G01N 21/85*    (2006.01)
    *G01N 33/18*    (2006.01)

(56) References Cited

U.S. PATENT DOCUMENTS

2018/0372608 A1* 12/2018 Park .................. C12Q 1/18
2020/0116618 A1   4/2020 Park et al.
2021/0080369 A1   3/2021 Kim et al.

FOREIGN PATENT DOCUMENTS

| | | |
|---|---|---|
| KR | 10-2018-0048456 A | 5/2018 |
| KR | 10-1920852 B1 | 11/2018 |
| KR | 10-1939779 B1 | 1/2019 |
| WO | 2016/191646 A2 | 12/2016 |
| WO | 2019/221557 A1 | 11/2019 |

OTHER PUBLICATIONS

Application No. PCT/KR2020012995, Extended European Search Report, Mailed Jan. 4, 2024, 8 pages.

* cited by examiner

DEVICE FOR WATER EXAMINATION

TECHNICAL FIELD

One or more embodiments of the present disclosure relate to a water examination device.

BACKGROUND ART

In general, a fluid such as water or beverage is supplied to a user through various treatments such as filtration. In the case of a fluid intended for drinking, substances other than additives that are added in the fluid as necessary, for example, microorganisms, etc., should be removed and then the fluid is supplied to the user. However, in the process of processing the fluid, microorganisms in the fluid may unintentionally proliferate due to circumstances such as contact with external air.

Although various methods have been proposed in the related art to detect microorganisms in a fluid and inspect water quality, it is very difficult to detect a very small amount of microorganisms in a fluid.

DESCRIPTION OF EMBODIMENTS

Technical Problem

In order to address above-described issues and/or limitations, the present disclosure provides a water examination device that examines water quality by detecting microorganisms in a fluid in real-time using a chaotic wave sensor.

Technical Solution to Problem

According to an embodiment of the present disclosure, a water examination device includes: a main body; a cup accommodation unit formed inward from a surface of the main body such that a cup containing a fluid is accommodated therein; a wave source for irradiating a wave toward the cup accommodation unit; a detector for detecting a laser speckle generated when the irradiated wave is multiple-scattered in the fluid, at every time point set in advance; and a controller for estimating whether foreign substances exist in the fluid in real-time by using the detected laser speckle.

Advantageous Effects of Disclosure

A water examination device according to one or more embodiments of the present disclosure may examine water quality, by estimating whether there are microorganisms in a fluid and/or a concentration of microorganisms rapidly at low costs by using a change in a temporal correlation or a spatial correlation of laser speckles.

BEST MODE

Figure 1:
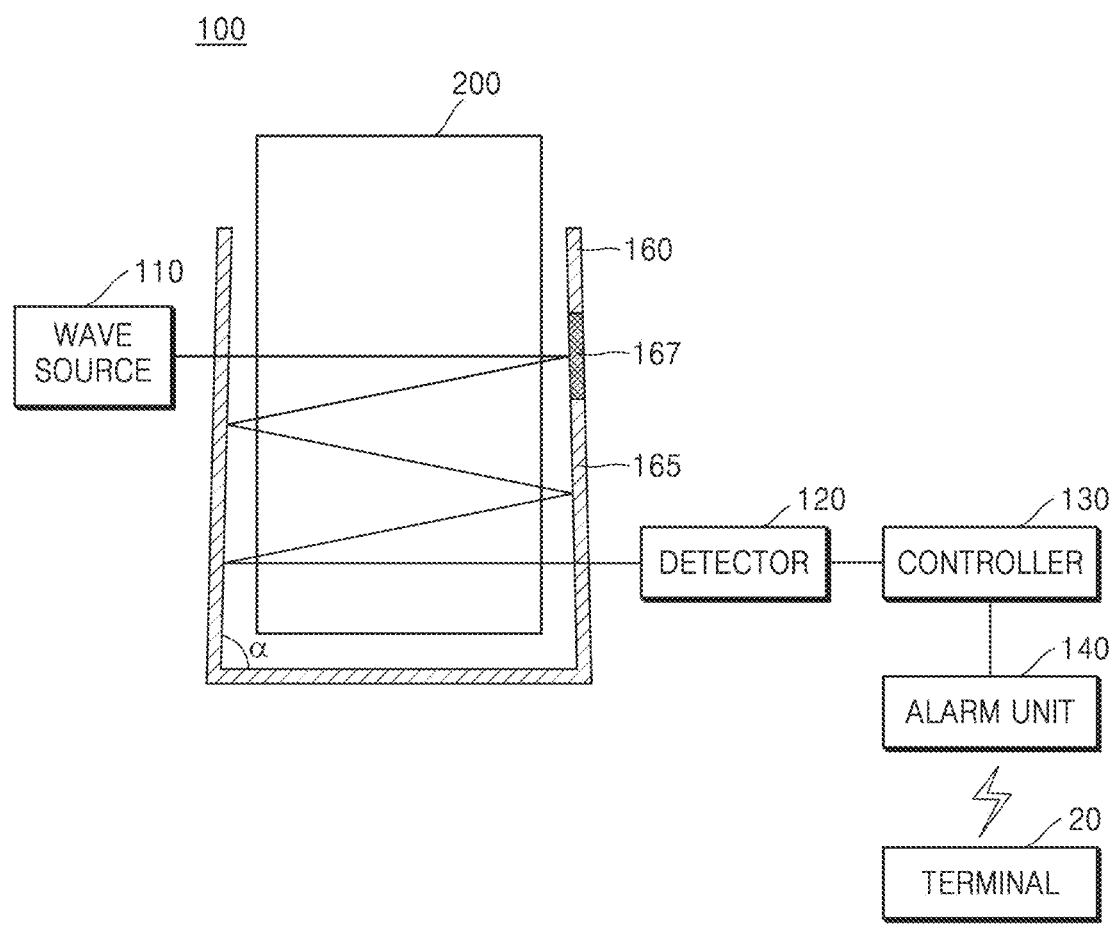
FIG. 1 is a conceptual diagram schematically showing a water examination device according to an embodiment of the present disclosure.

According to an embodiment of the present disclosure, a water examination device includes: a main body; a cup accommodation unit formed inward from a surface of the main body such that a cup containing a fluid is accommodated therein; a wave source for irradiating a wave toward the cup accommodation unit; a detector for detecting a laser speckle generated when the irradiated wave is multiple-scattered in the fluid, at every time point set in advance; and a controller for estimating whether foreign substances exist in the fluid in real-time by using the detected laser speckle.

According to an embodiment of the present disclosure, the cup accommodation unit may include: a bottom portion formed in the main body; and a wall portion extending from the bottom portion toward the surface of the main body and formed to surround at least a part of a side surface of a cup accommodated in the cup accommodation unit.

According to an embodiment of the present disclosure, an angle between the bottom portion and the wall portion may not be a right angle.

According to an embodiment of the present disclosure, the angle may range from 85° to 88°.

According to an embodiment of the present disclosure, the wall portion may be formed to have an annular shape and may be formed to be narrowed toward the surface of the main body.

According to an embodiment of the present disclosure, three or more support portions may protrude from the bottom portion.

According to an embodiment of the present disclosure, each of the three or more support portions and the cup may be in a point-contact with each other.

According to an embodiment of the present disclosure, the bottom portion or the wall portion may include a multi-scattering amplification region for amplifying a number of times that the wave irradiated from the wave source is multiple scattered in the fluid.

According to an embodiment of the present disclosure, the multi-scattering amplification region ay amplify the number of multiple scattering in the fluid by reflecting at least some of the wave emitted from the fluid onto the fluid.

According to an embodiment of the present disclosure, the controller may obtain a temporal correlation of the detected laser speckle by using the detected laser speckle, and may estimate whether microorganisms exist in the fluid in real-time based on the obtained temporal correlation.

According to an embodiment of the present disclosure, the temporal correlation may include a difference between first image information of the laser speckle detected at a first time point and second image information of the laser speckle detected at a second time point that is different from the first time point.

According to an embodiment of the present disclosure, the first image information and the second image information may include at least one of pattern information of the laser speckle and intensity information of the wave.

According to an embodiment of the present disclosure, the controller may obtain a spatial correlation of an interference pattern of an optical image detected by the detector, and determine whether microorganisms exist in the fluid based on a change in the spatial correlation of the interference pattern over time.

According to another embodiment of the present disclosure, a water examination method includes: inserting a cup in which a fluid is capable of being accommodated into a cup accommodation unit; irradiating, by a wave source, a wave having coherence to the cup accommodation unit, in which the cup is accommodated; detecting, by a detector, a laser speckle generated when the wave irradiated from the wave source is multiple scattered in the fluid, at every time point set in advance; and estimating, by a controller, whether microorganisms exist in the fluid in real-time by using the detected laser speckle.

Other aspects, features and advantages of the disclosure will become better understood through the accompanying drawings, the claims and the detailed description.

MODE OF DISCLOSURE

The exemplary embodiments will be described below in more detail with reference to the accompanying drawings. Those components that are the same or are in correspondence are rendered the same reference numeral regardless of the figure number, and redundant explanations are omitted.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a unit, region, or component is referred to as being "formed on" another layer, region, or component, it can be directly or indirectly formed on the other layer, region, or component. That is, for example, intervening units, regions, or components may be present.

It will be understood that when an element is referred to as being "connected" or "coupled" to another element, it can be directly connected or coupled to the other element or intervening elements may be present.

It will be further understood that the terms "comprises," "comprising," "includes" and/or "including," when used herein, specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

Figure 2:
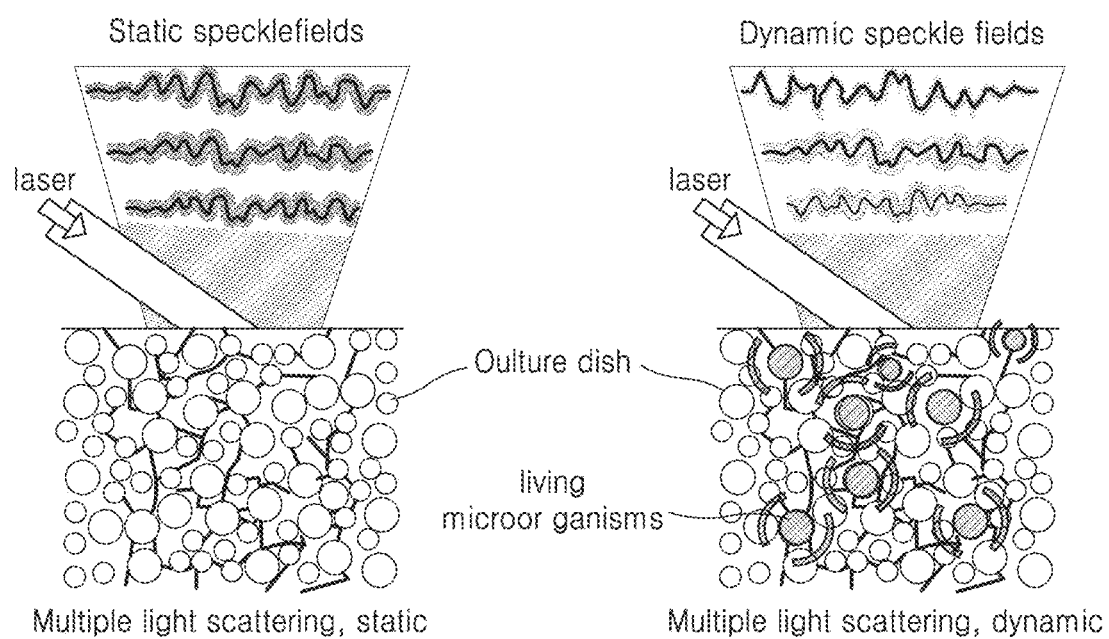
FIG. 2 is a diagram illustrating principles of a chaotic wave sensor according to an embodiment of the present disclosure.
Figure 3:
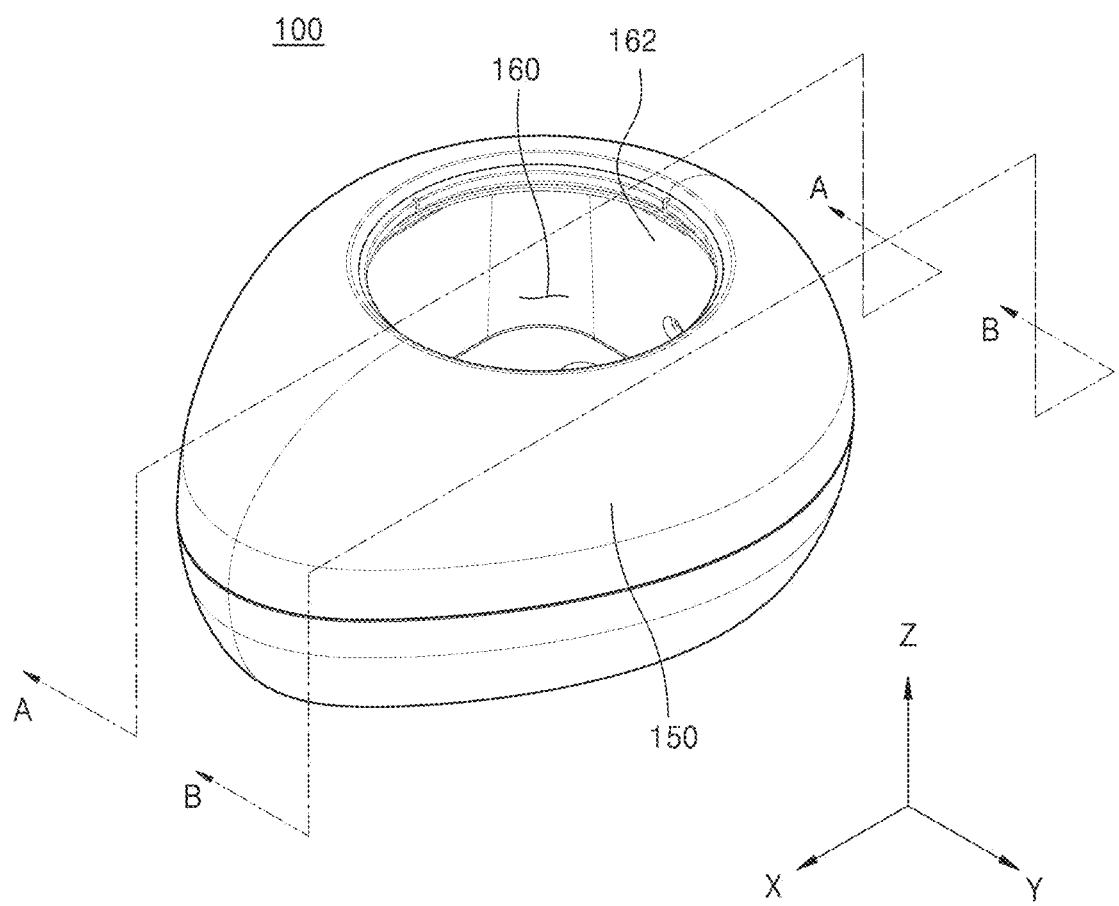
FIG. 3 is a perspective view of a water examination device which is actually implemented from the conceptual diagram of FIG. 1.
Figure 4:
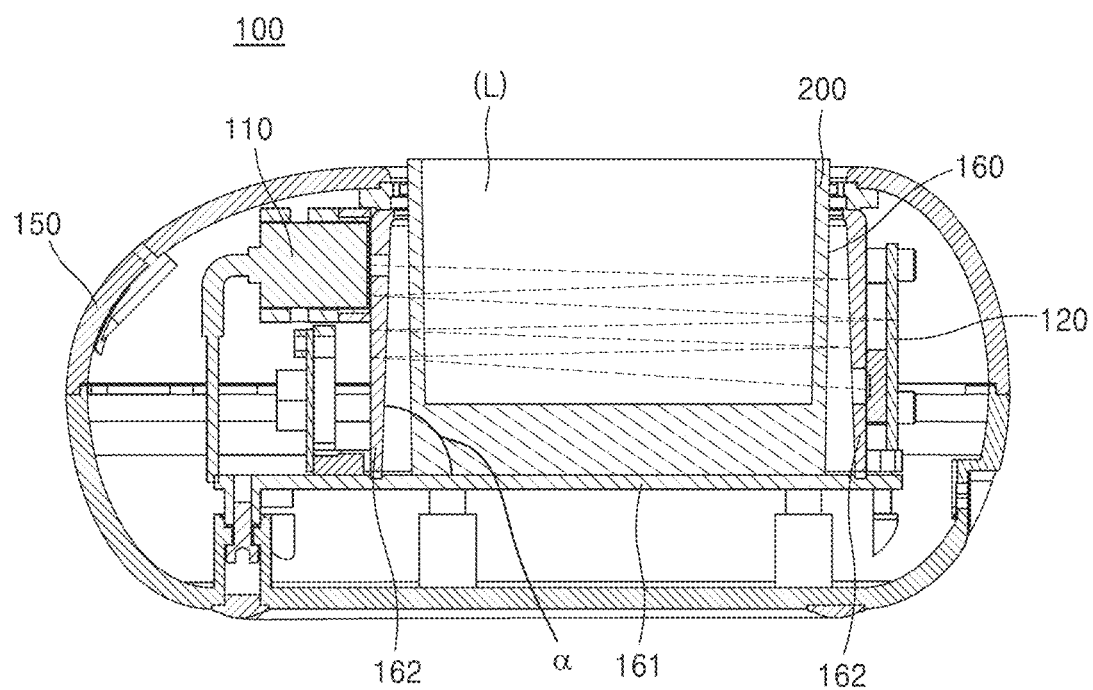
FIG. 4 is a cross-sectional view taken along line A-A of FIG. 3, and shows a state in which a cup is accommodated in a cup accommodation unit.
Figure 5:
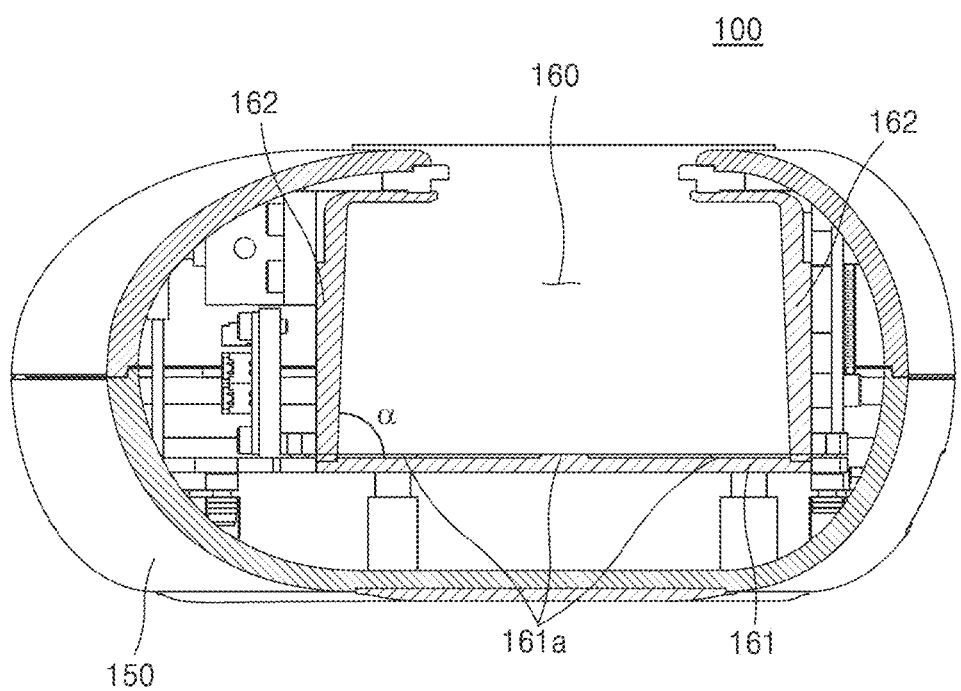
FIG. 5 is a cross-sectional view taken along line B-B of FIG. 3.
Figure 6:
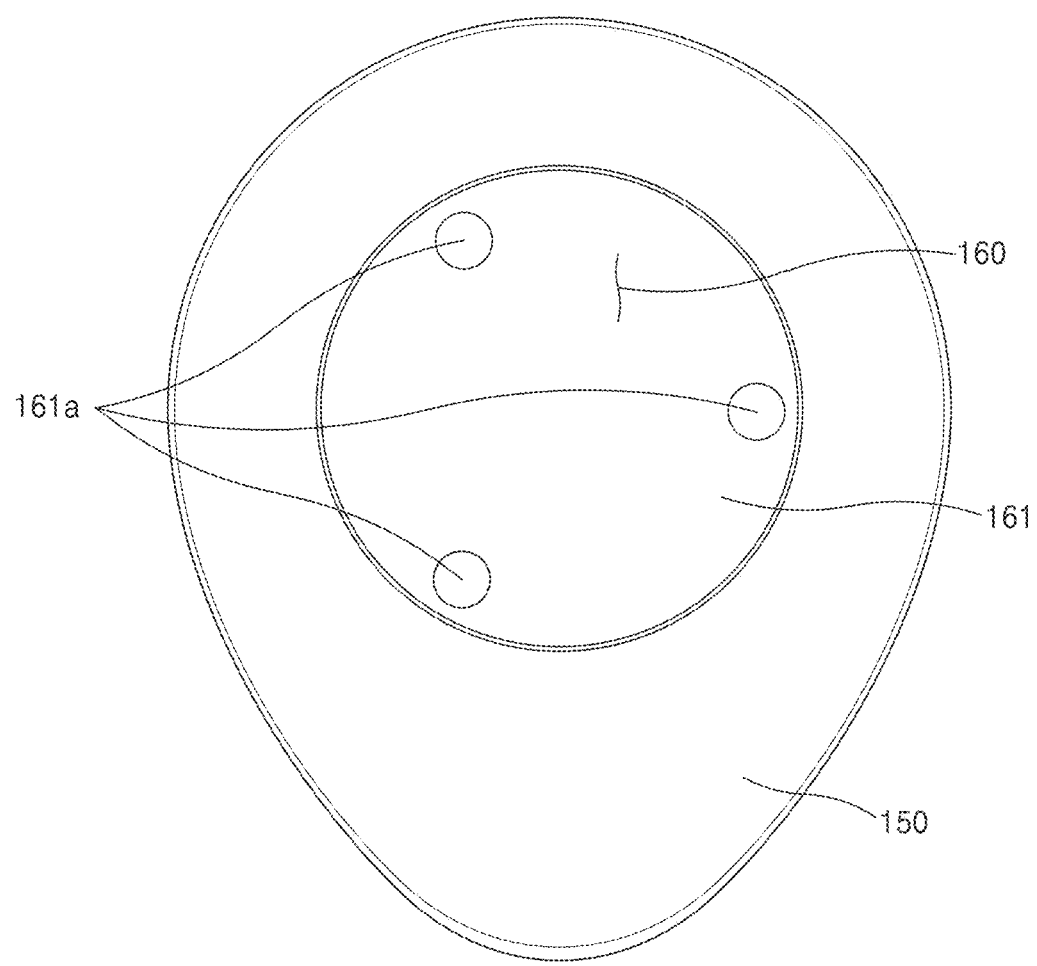
FIG. 6 is a plan view of the water examination device of FIG. 3.
Figure 7:
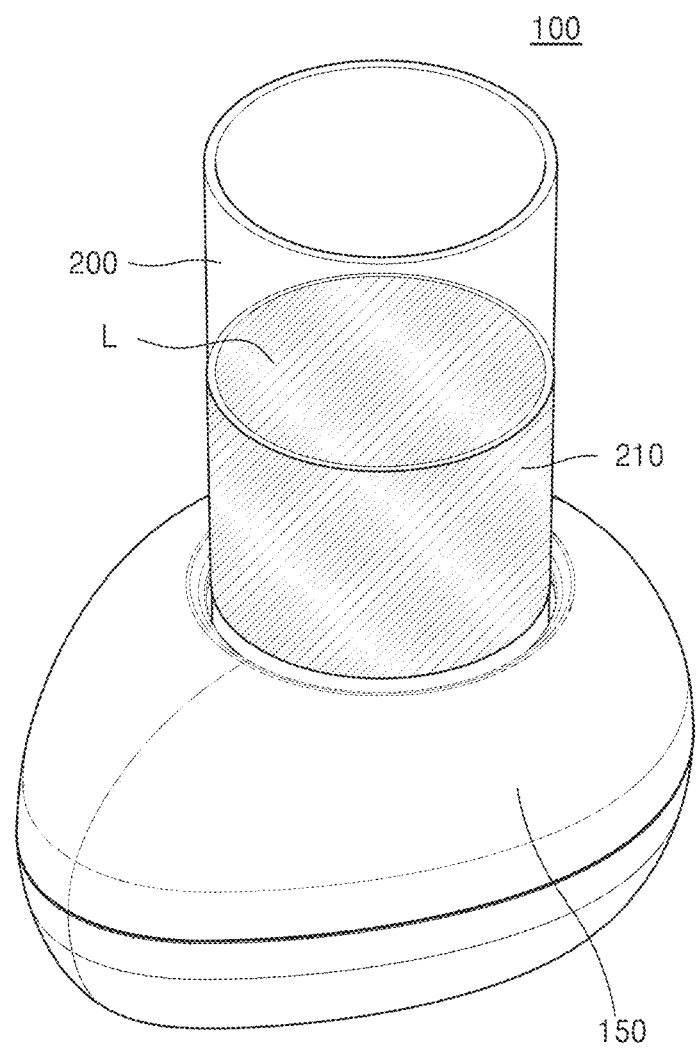
FIG. 7 is a perspective view showing a cup mounted in the cup accommodation unit of FIG. 3.

FIG. 1 is a conceptual diagram schematically showing a water examination device 100 according to an embodiment of the present disclosure, and FIG. 2 is a diagram for describing principles of a chaotic wave sensor according to an embodiment of the present disclosure. In addition, FIG. 3 is a perspective view of a water examination device actually implemented from the conceptual diagram of FIG. 1, FIG. 4 is a cross-sectional view taken along line A-A of FIG. 3 and shows a state in which a cup is accommodated in a cup accommodation unit, FIG. 5 is a cross-sectional view taken along line B-B of FIG. 3, FIG. 6 is a plan view of the water examination device of FIG. 3, and FIG. 7 is a perspective view showing a cup mounted in the cup accommodation unit of FIG. 3.

Referring to FIG. 1, the water examination device 100 according to an embodiment of the present disclosure may include a wave source 110, a detector 120, and a controller 130. In addition, the water examination device 100 of FIG. 1 may further include an alarm unit 140 and a cup accommodation unit 160 (see FIG. 4). In addition, a cup 200 containing a fluid L that is an object to be examined may be accommodated in the cup accommodation unit 160. Also, the cup accommodation unit 160 may include a multi-scattering amplification region 165 for amplifying the number of times that the wave irradiated from the wave source 110 is multiple scattered in the fluid L.

Here, the fluid L may be a liquid or a gas. In addition, the fluid L may be a material in which microorganisms may proliferate, for example, water that does not contain a scattering material therein. However, the present disclosure is not limited thereto, and in another embodiment, the fluid L may be a material such as milk having a scattering material therein. Hereinafter, for convenience of description, a case in which the fluid L does not include the scattering material will be described first, and the fluid L including the scattering material will be described later.

The wave source 110 may irradiate a wave toward the fluid L in the cup 200 accommodated in the cup accommodation unit 160. The wave source 110 may include all kinds of source devices capable of generating waves, for example, may be a laser capable of irradiating light of a certain wavelength band.

The detector 120 may detect whether there are microorganisms M, e.g., impurities, in the fluid L, by using the wave. In the present specification, the detector 120 may include a chaotic wave sensor. Here, the impurities may include insoluble suspended matters. The detector 120 may also execute a function of detecting impurities included in the fluid L, as well as the microorganisms M. However, for convenience of description, the case of detecting the microorganism (M) in the fluid (L) will be described below.

Hereinafter, the principle of the chaotic wave sensor of the present disclosure will be described with reference to FIG. 2.

When light is irradiated to a material having a uniform internal refractive index, e.g., glass, the light is refracted in a constant direction. However, when coherent light such as a laser is irradiated to a material having non-uniform internal refractive index, multiple scattering that is very complicated occurs in the material.

Referring to FIG. 2, in light or wave (hereinafter, referred to as wave for convenience' sake) irradiated from a wave source 110, some of the waves scattered through complicated paths due to the multiple scattering passes through a test target surface. Waves passing through multiple points in the test target surface generate constructive interference or destructive interference, and the constructive/destructive interference of the waves generates grain patterns (speckles).

In the present specification, the waves scattered in the complicated paths are referred to as "chaotic wave", and the chaotic wave may be detected through laser speckles.

A left side of FIG. 2 shows a state in which a laser is irradiated to a stabilized medium. When interference light (e.g., laser) is irradiated to the stabilized medium, in which internal component material does not move, a stabilized speckle pattern without a variation may be observed.

However, as shown at a right side of FIG. 2, when the medium having non-stabilized internal component that is moving, such as bacteria, is included, the speckle pattern varies.

That is, an optical path may be minutely changed over time due to minute biological activities of living things (e.g., intracellular movement, movement of microorganisms, movement of mites, etc.). Because the speckle pattern is generated due to interference of the waves, a minute change in the optical path may cause a variation in the speckle pattern. Accordingly, when a temporal variation in the speckle pattern is measured, movements of living things may be rapidly measured. As described above, when the variation in the speckle pattern according to time is measured, existence of the living things and concentration of the living things may be identified, and further, kinds of the living things may be identified.

In the present specification, a structure for measuring the variation in the speckle pattern is defined as a chaotic wave sensor.

On the other hand, because the fluid L such as water does not contain a homogeneous material that generates scattering therein as described above, when the microorganisms M are not present, the laser speckle may not be generated. However, the water examination device 100 according to the embodiment of the present disclosure may generate a stabilized laser speckle pattern by multi-scattering waves through a multi-scattering amplification region 165 that will be described later. According to the water examination device 100, when there are the microorganisms M in the fluid L contained in the cup 200, the path of the wave may be minutely changed by the movement of the microorganisms. The minute change in the wave path may cause a change in the speckle pattern, and accordingly, by measuring the temporal change of the speckle pattern, the presence or absence of the microorganisms M in the fluid L may be rapidly detected.

Referring back to FIGS. 1 and 2, the water examination device 100 according to the embodiment of the present disclosure may include the wave source 110, the detector 120, and the controller 130.

The wave source 110 may irradiate a wave toward the fluid L in the cup 200 accommodated in the cup accommodation unit 160. The wave source 110 may include all kinds of source devices capable of generating waves, for example, may be a laser capable of irradiating light of a certain wavelength band. Although the present disclosure is not limited to the kind of wave source, for convenience of description, a case in which the wave source is a laser will be described below.

For example, the laser having excellent coherence may be used as the wave source 110 in order to form speckles in the fluid L. Here, when a spectral bandwidth of the wave source is shorter, a measuring accuracy may increase, wherein the spectral bandwidth determines the coherence of the laser wave source. That is, when a coherence length increases, the measuring accuracy also increases. Accordingly, a wave source irradiating the laser having a spectral bandwidth that is less than a reference bandwidth set in advance may be used as the wave source 110, and when the spectral bandwidth is reduced shorter than the reference bandwidth, the measuring accuracy may increase. For example, the spectral bandwidth of the wave source may be set to satisfy following condition of Equation 1 below.

$$\text{Spectral bandwidth} < 5 \text{ nm} \qquad \text{[Equation 1]}$$

According to Equation 1 above, when the light is irradiated into the fluid at every reference time in order to measure a variation in the laser speckle pattern, the spectral bandwidth of the wave source 110 may be maintained to be less than 5 nm.

The detector 120 may detect the laser speckle generated by the irradiated wave multi-scattered in the fluid L at every preset time point. Here, the time point may denote one instant during continuous flow of time, and time points may be set in advance with constant time intervals therebetween, but are not limited thereto, that is, may be set in advance with an arbitrary time interval. The detector 120 may include a sensing unit corresponding to the kind of the wave source 110, for example, a CCD camera that is an imaging device in a case where a light source of a visible ray wavelength band is used. The detector 120 may detect the laser speckle at a first time point at least, and may detect the laser speckle at a second time point, and then, may provide the controller 130 with the detected laser speckles. The first time point and the second time point are just examples selected for convenience of description, and the detector 120 may detect laser speckles at a plurality of time points more than the first and second time points.

In detail, when the wave is irradiated to the fluid L, the incident wave may generate laser speckle due to the multiple scattering. The laser speckle is generated by the light interference effect, and thus, when there is no microorganism in the fluid L, a constant interference pattern may be shown over time due to the multi-scattering amplification region. As compared with this, when microorganisms exist in the fluid L, the laser speckle may vary over time due to the movement of the microorganisms M. The detector 120 detects the laser speckle varying over the time at every time point set in advance, to provide the laser speckle to the controller 130. The detector 120 may detect the laser speckle at a sufficient speed to sense the movement of the microorganisms M, for example, 25 frames to 30 frames per second.

In addition, in a case where the image sensor is used as the detector 120, the image sensor may be arranged so that a size d of one pixel in the image sensor is equal to or less than a grain size of the speckle pattern. For example, the image sensor may be arranged in an optical system included in the detector 120 to satisfy the condition of Equation 2 below.

$$d \leq \text{speckle grain size} \qquad \text{[Equation 2]}$$

As expressed by Equation 2 above, the size d of one pixel in the image sensor has to be equal to or less than the grain size of the speckle pattern, but when the size of the pixel is too small, an undersampling may occur and it may be difficult to utilize the pixel resolution. Accordingly, in order to achieve an effective signal to noise ratio (SNR), the image sensor may be arranged such that maximum five pixels correspond to the speckle grain size.

The controller 130 may obtain a temporal correlation of the detected laser speckle, by using the detected laser speckle. The controller 130 may estimate, in real-time, the existence of the microorganisms in the fluid L, based on the obtained temporal correlation. In the present specification, real-time denotes estimating whether the microorganisms M exist within three seconds, for example, the existence of the microorganisms M may be estimated within one second.

In an embodiment, the controller 130 may estimate whether the microorganisms M exist by using a difference between first image information of the laser speckle detected at a first time point and second image information of the laser speckle detected at a second time point that is different from the first time point. Here, the first image information and the second image information may include at least one of laser speckle pattern information and wave intensity information.

In addition, according to the embodiment, the difference between the first image information at the first time point and the second image information at the second time point is not only used, but image information of a plurality of laser speckles at a plurality of time points may be also used. The controller 130 may calculate a temporal correlation coefficient between the images by using image information of the laser speckles generated at the plurality of time points set in advance, and may estimate existence of the microorganisms M in the fluid L based on the temporal correlation coefficient. The temporal correlation between the detected laser speckle images may be calculated by using Equation 3 below.

$$\overline{C}(x, y; \tau) = \frac{1}{T-\tau}\sum_{t=1}^{T-\tau} \overline{I}(x, y; t)\overline{I}(x, y; t+\tau)\delta t \quad \text{[Equation 3]}$$

In Equation 3 above, $\overline{c}$ denotes the temporal correlation coefficient, $\overline{I}$ denotes a normalized light intensity, (x,y) denotes a pixel coordinate of the camera, t denotes a measured time, T denotes a total measured time, and $\tau$ denotes a time lag.

According to Equation 3 above, the temporal correlation coefficient may be calculated, and in an embodiment, the existence of the microorganisms may be estimated by analyzing whether the temporal correlation coefficient is below a reference value set in advance. In more detail, when the temporal correlation coefficient is below the reference value beyond an error range set in advance, it may be estimated that the microorganisms exist.

In addition, the detector 120 may estimate a concentration of impurities in the fluid L accommodated in the cup 200. Here, the detector 120 may perform a function of measuring a turbidity of the fluid L by estimating the concentration of the impurities in the fluid L. It is difficult to measure an impurity concentration of 105 cfu/ml or less by using a general turbidity measurement device. However, the detector 120 according to the embodiment of the present disclosure may measure the impurity concentration of 106 cfu/ml or less by using a method of determining a concentration of the impurities as described below. Here, impurities are not limited to microorganisms. Hereinafter, for convenience of description, a method of determining the concentration of the impurities by using the laser speckle in the controller 130 will be described in detail below, based on the case in which the impurities include the microorganisms.

The controller 130 may calculate a standard deviation of light intensity of the laser speckle, on a laser speckle image measured at every reference time. As the microorganisms included in the fluid L continuously move, constructive interference and destructive interference may vary according to the movements. Here, when the constructive interference and the destructive interference change, the light intensity may largely change. Then, the controller 130 may calculate the standard deviation representing the variation degree of the light intensity, to detect the microorganisms in the cup 200, and may measure the distribution of the microorganisms.

For example, the controller 130 may combine the laser speckle image at every time point determined in advance, and may calculate the standard deviation of the light intensity of the laser speckle over time in the combined image. The standard deviation of the light intensity of the laser speckle over time may be calculated by using Equation 4 below.

$$S(x, y) = \sqrt{\frac{1}{T}\sum_{t=1}^{T}(I_t(x, y) - \overline{I})^2} \quad \text{[Equation 4]}$$

In Equation 4 above, S denotes the standard deviation, (x,y) denotes a pixel coordinate of the camera, T denotes a total measurement time, t denotes a measurement time, $I_t$ denotes a light intensity measured at the time t, and $\overline{I}$ denotes an average light intensity according to time.

The constructive and destructive interferences may vary depending on the movements of the microorganisms, and the standard deviation value calculated according to the Equation 4 increases. Thus, the concentration of the microorganisms may be measured based on the standard deviation value. However, the present disclosure is not limited to the method of measuring the concentration of microorganisms by using Equation 4 above, and the concentration of microorganisms may be measured by any method using a difference in the detected laser speckle.

In addition, the controller 130 may measure distribution, that is, concentration of the microorganisms included in the fluid, based on a linear relationship between a magnitude of the standard deviation value of the laser speckle light intensity and the concentration of the microorganisms.

The multi-scattering amplification region 165 may amplify the number of multiple scattering in the fluid L by reflecting at least some of the waves emitted from the fluid L toward the fluid L again. The multi-scattering amplification region 165 may include a multiple scattering material. For example, the multiple scattering material may include a particle having a diameter equal to or less than a micrometer and having a large refractive index, for example, titanium oxide ($TiO_2$) nano-particles. Here, the multi-scattering amplification region 165 may be formed by coating the multiple scattering material on surfaces of a bottom portion 161 (see FIG. 4) and a wall portion 162 (see FIG. 4) of the cup accommodation unit 160. However, the present disclosure is not limited thereto, and in another embodiment, the multi-scattering amplification region 165 is formed by including the multiple scattering material in the bottom portion 161 (see FIG. 4) and the wall portion 162 (see FIG. 4).

In addition, at least a part of the multi-scattering amplification region 165 may be provided as a reflection region 167 that reflects all of the waves emitted from the fluid L to the fluid L. The reflection region 167 may reduce the emission of waves to outside of the water examination device 100 from the fluid L, so as to amplify a microorganism detecting rate of the detector 120. The reflection region 167 may be disposed to face an incident region where the wave from the wave source 110 is incident. The reflection region 167 reflects all of the waves irradiated from the wave source 110 into the fluid L, and thus, an amount of waves that may be multiple scattered in the fluid L may be increased. As such, the microorganism sensing rate of the detector 120 may be amplified. In another embodiment, an entire area of the multi-scattering amplification region 165, rather than a moving path of the waves emitted toward the detector 120, may include the reflection region.

Referring back to FIG. 1, the water examination device 100 according to an embodiment of the present disclosure may further include the alarm unit 140. In addition, the water examination device 100 may be connected to a terminal 20 outside or a server (not shown) via a network.

When a signal t1 indicating the existence of microorganisms is input from the controller 130, the alarm unit 140 may notify a user of the signal. The alarm unit 140 may notify that the microorganisms exist in the fluid by using at least one of sound and light. The alarm unit 140 may include a lighting unit such as an LED for generating a warning signal via light and a speaker (not shown) for generating a warning signal via sound, and the light and sound may be generated at the same time.

In addition, the water examination device 100 may further include a communication unit (not shown) that may communicate with the terminal 20 of a user. When the signal t1 indicating the existence of microorganisms is input from the controller 130, the alarm unit 140 may provide the terminal 20 with information including the microorganism sensing signal through a wireless or wired communication unit (not shown). Also, although not shown in the drawing, the alarm unit 140 may provide the above information to a server (not shown). When the information about whether the microorganisms are sensed, the time of sensing the microorganisms, and the concentration of the microorganisms is uploaded through the alarm unit 140, the water examination device 100 registers the information on the server (not shown) and provides an interface through which other users may search for the data registered on the server (not shown). The water examination device 100 according to the embodiment may establish a situation in which microorganisms are generated, etc. as a database through the above processes. The terminal 20 may include a personal computer or a portable terminal on which a Web service may be used under a wired/wireless communication environment.

Referring to FIGS. 3 to 7, the water examination device 100 according to the embodiment of the present disclosure may include the wave source 110, the detector 120, a main body 150, and the cup accommodation unit 160. In addition, although not shown in FIGS. 3 to 7, the water examination device 100 may further include the controller 130 (see FIG. 1) and the alarm unit 140 (see FIG. 1) described with reference to FIG. 1. Here, since the wave source 110 and the detector 120 are described in FIG. 1, etc., detailed descriptions thereof will be omitted.

The main body 150 forms the outer appearance of the water examination device 100, and the wave source 110, the detector 120, and the cup accommodation unit 160 may be provided in the main body 150. In the drawings, the main body 150 forms an eccentric streamlined shape (or an egg-like shape when viewed from above) as a whole, and the cup accommodation unit 160, in which the cup 200 may be fitted therein from the upper portion thereof, is formed. However, the present disclosure is not limited thereto, a size, a shape, and a material of the main body 150 or a location in the main body 150, where the cup accommodation unit 160 is formed, may be variously changed.

The cup accommodation unit 160 may be formed such that the cup 200 may be fitted therein from the upper portion of the main body 150 to the inside (e.g., the center side). The cup accommodation unit 160 may include the bottom portion 161 and the wall portion 162. In other words, it may be expressed that the cup accommodation unit 160 in which the cup 200 may be accommodated and mounted is formed by the bottom portion 161 and the wall portion 162.

The bottom portion 161 forms a bottom surface of the cup accommodation unit 160 and has a substantially flat shape. The multi-scattering amplification region 165 described above may be formed in at least a part of the bottom portion 161.

Here, in the water examination device 100 according to the embodiment of the present disclosure, three or more support portions 161a protrude from the bottom portion 161 so as to stably support the cup 200 accommodated in the cup accommodation unit 160.

In detail, the cup 200 containing the fluid has various shapes, some of which may not have flat bottom surfaces. In this case, when the cup 200 is seated in the cup accommodation unit 160, the cup 200 may not stop and be minutely shaken, and there may be an error in the measurement value.

In order to address the above issue, according to the embodiment of the present disclosure, three or more support portions 161a protrude from the bottom portion 161 so as to stably support the cup 200 accommodated in the cup accommodation unit 160.

When three or more support portions 161a protrude from the bottom portion 161 as described above, the bottom portion 161 and the bottom surface of the cup 200 come into contact with each other at three (or more) points, rather than a surface contact, and through the above three-point contact, the shaking of the cup 200 that may occur when the bottom surface of the cup 200 is not flat may be reduced, thereby improving a precision during repeated measurements.

In addition, the wall portion 162 is nearly perpendicular to the bottom portion 161, and has an annular shape so that the cup 200 may be accommodated therein. The multi-scattering amplification region 165 and/or the reflection region 167 described above may be formed in at least a part of the wall portion 162.

Here, in the water examination device 100 according to the embodiment of the present disclosure, an angle α between the wall portion 162 and the bottom portion 161 is not exactly a right angle, but is slightly inclined (i.e., obliquely).

In detail, the water examination device 100 according to the embodiment of the present disclosure has a structure, in which a portion where the cup accommodation unit 160 is formed, is opened in order to accommodate the cup 200. When the light is scattered due to the laser reflection in the structure in which one surface (at least a part of which) is opened as described above, some of the scattered light is emitted to outside of the opened structure, and there is a loss in the light intensity received by the detector 120 (see FIG. 1) and a result obtained through the light scattering analysis is affected.

In order to address the above issue, according to the embodiment of the present disclosure, the angle α between the wall portion 162 and the bottom portion 161 is not exactly a right angle, but is slightly inclined. That is, the wall portion 162 is formed such that the angle α between the wall portion 162 and the bottom portion 161 is about 85° to 88°, and the laser reflected by the wall portion 162 may proceed opposite to the opened surface to reduce the loss in the light intensity. Thus, the light scattering effect may be improved.

In other words, it may be expressed that the wall portion 162 is formed to have an entrance that gradually narrows upward (that is, in a +Z axis direction), or it may be expressed that a diameter thereof is gradually reduced upward. According to the present disclosure as described above, the loss in the light emitted from the wave source 110 to outside is reduced, and the light scattering effect may be improved.

Meanwhile, the cup 200 may include an opaque portion 210. In detail, when the surface of the cup 200 is entirely transparent, the laser is exposed to outside, and then, a glaring effect may occur to the user. In addition, there is a need to indicate a minimum amount of fluid that is necessary for inspecting water quality of the fluid in the cup 200 by using the water examination device 100.

In order to address the above issue, the opaque portion 210 is formed in at least a part of the cup 200, in particular, to a certain height in the lower portion of the side surface of the cup 200, and thus, the minimum amount of fluid that is necessary for inspecting the water quality of the fluid is indicated to the user, and at the same time, the user may not directly see the laser.

Figure 8A:
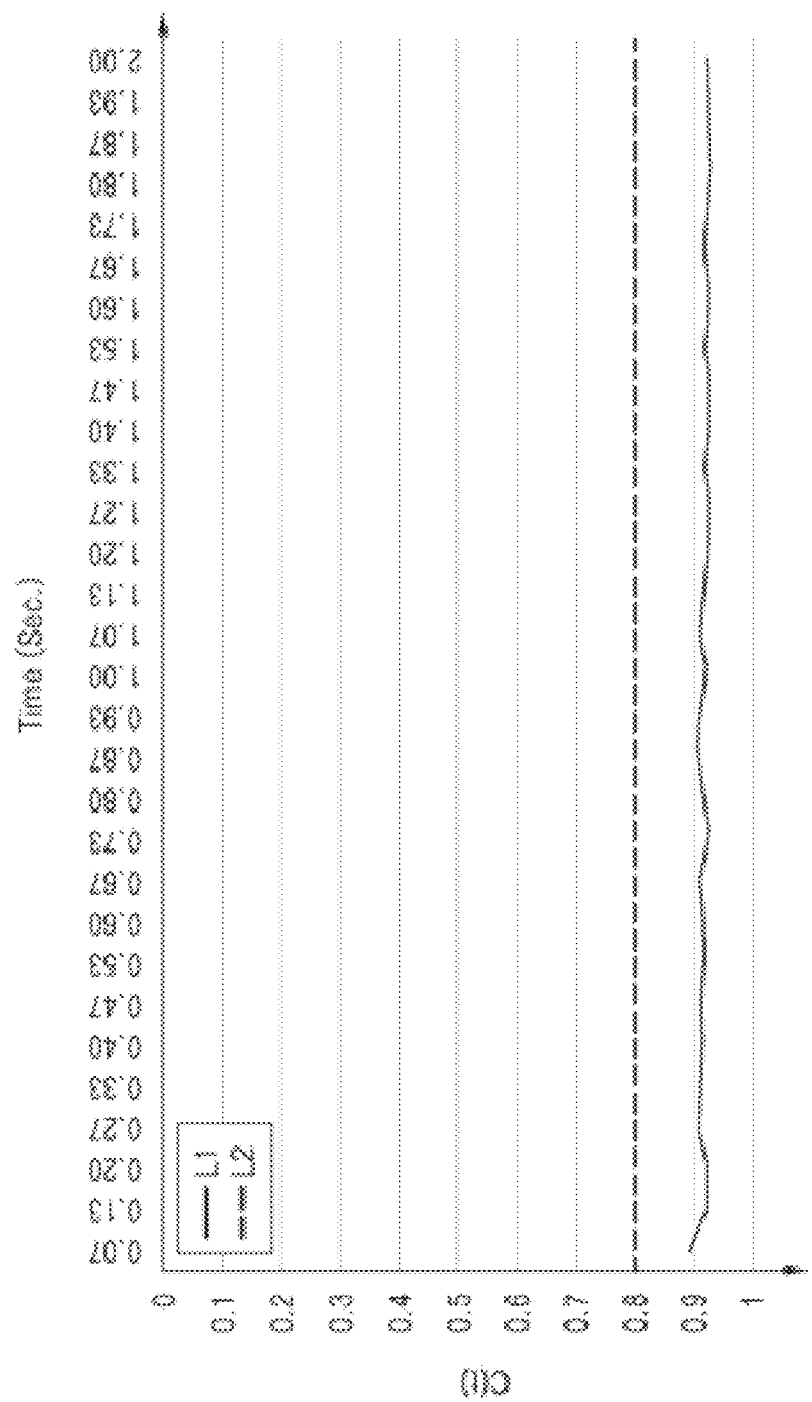
FIGS. 8A to 8C are graphs showing temporal correlation coefficients according to a bacterial concentration in a fluid in a water examination device according to an embodiment of the present disclosure.
Figure 8B:
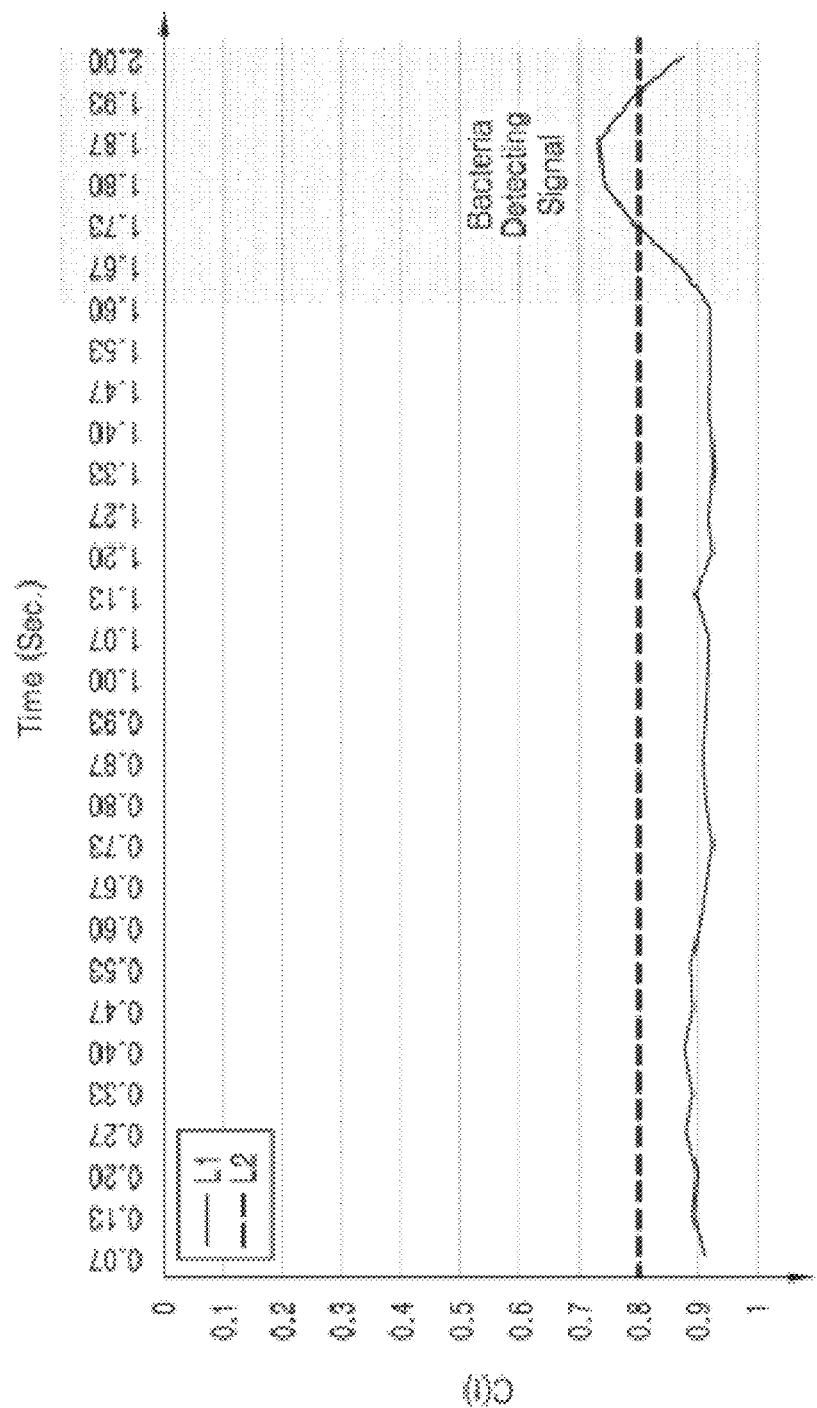
Figure 8C:
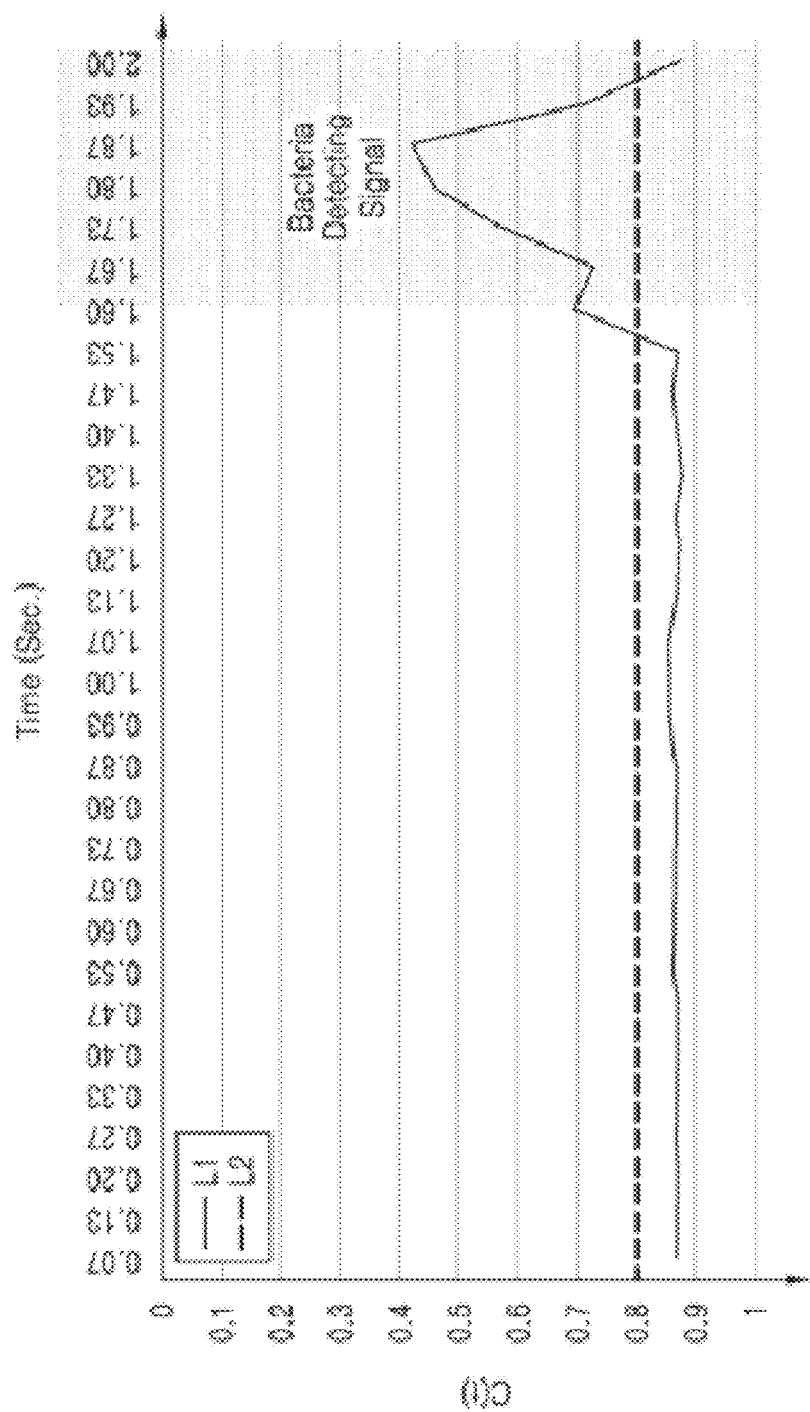

FIGS. 8A to 8C are graphs showing temporal correlation coefficients according to a bacterial concentration in a fluid in a water examination device according to an embodiment of the present disclosure. FIGS. 8A to 8C show a variation in the temporal correlation coefficient according to a concentration of microorganisms, when the microorganisms are artificially introduced into the fluid contained in the cup 200.

In the graphs of FIGS. 8A to 8C, an x-axis denotes time (t) and a y-axis denotes a temporal correlation coefficient (C(t)). Here, a dashed line L2 represents a reference value of the temporal correlation coefficient of the laser speckle set in advance in the detector 120. In addition, a solid line L1 represents measurement data of the temporal correlation coefficient of the laser speckle obtained by the detector 120 over time.

In FIG. 8A, the solid line L1 denotes the temporal correlation coefficient of the laser speckle obtained by the detector 120 when the microorganisms are not introduced in the fluid. Referring to FIG. 8A, when there is no microorganism in the fluid, there is no variation in the laser speckle that is generated due to scattering in the fluid, and thus, the temporal correlation coefficient is nearly consistent over time and does not exceed the reference value (L1) set in advance.

The solid line L1 of FIG. 8B indicates the temporal correlation coefficient of the laser speckle obtained through the detector 120 when 4 ml of microorganisms with a concentration of $10^0$ cfu/ml is introduced into the fluid. The solid line L1 of FIG. 8C indicates the temporal correlation coefficient of the laser speckle obtained through the detector 120 when 4 ml of microorganisms with a concentration of $10^0$ cfu/ml is introduced into the fluid.

Referring to FIGS. 8B and 8C, when the microorganisms exist in the fluid, the laser speckle generated due to the scattering in the fluid changes over time, and thus, the temporal correlation coefficient is changed at a time point when the microorganisms are sensed. Shaded areas (bacteria detecting signal) in FIGS. 8B and 8C indicate the change in the temporal correlation coefficient at the time point when the microorganisms are detected, and it may be identified that a peak value of the temporal correlation coefficient increases as the concentration of the microorganisms increases. Meanwhile, in the shaded areas of FIGS. 8B and 8C, the detector 120 may determine that the microorganisms exist when the temporal correlation coefficient (L1) of the laser speckle exceeds the dashed line L2 that is the reference value set in advance. Here, when there are the microorganisms, a time taken for the detector 120 to detect the microorganisms may include a period from the time point when the temporal correlation coefficient rapidly changes to a time point when the temporal correlation coefficient meets the dashed line L2, e.g., the reference value, and may be about 0.2 sec. or less based on FIGS. 8B and 8C.

As such, the water examination device according to the embodiments of the present disclosure may sense the microorganisms, e.g., impurities, in the fluid within a very short time period of 0.2 sec. or less, that is, in real-time. Also, the water examination device according to the embodiments of the present disclosure may estimate the concentration of the microorganisms by using a change rate or a peak value of the temporal correlation coefficient. In addition, it may be identified that the water examination device may detect microorganisms even when the concentration of the microorganisms is low ($10^0$ cfu/ml).

As described above, the water examination device according to the embodiments of the present disclosure may estimate the existence of the microorganisms in the fluid or the concentration of the microorganisms rapidly at low costs, by using the variation in the temporal correlation of the laser speckle.

Hereinafter, a method for detecting microorganisms in the water examination device according to another embodiment will be described below. According to the method of detecting microorganisms in the water examination device of another embodiment of the present disclosure, the existence or the concentration of the microorganisms in the fluid is detected by using a spatial correlation, instead of the temporal correlation. Hereinafter, the method will be described below in more detail.

Figure 9:
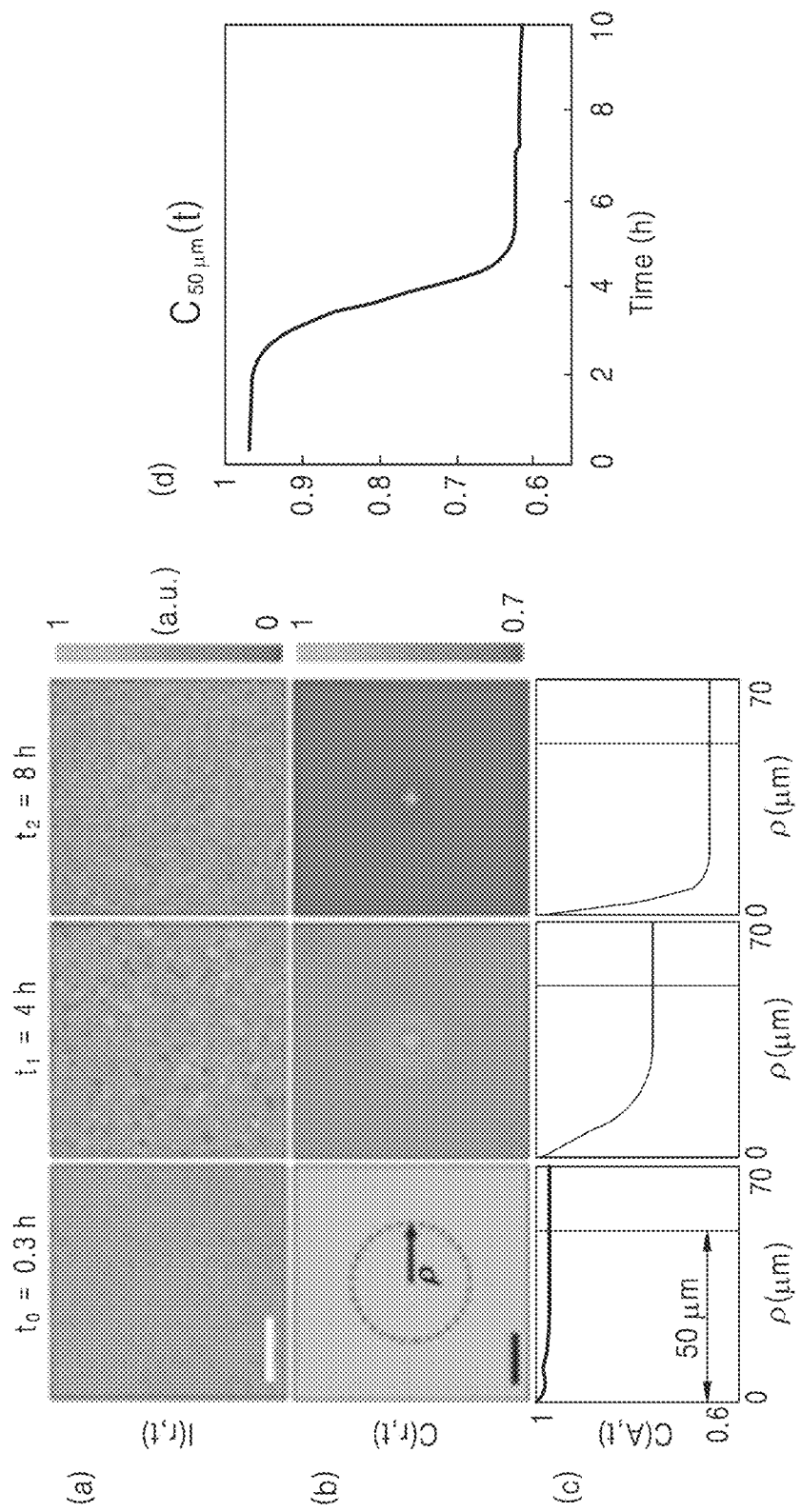
FIGS. 9 and 10 are diagrams for describing principles of determining concentration information of a high concentration sample in a water examination device according to another embodiment of the present disclosure.
Figure 10:
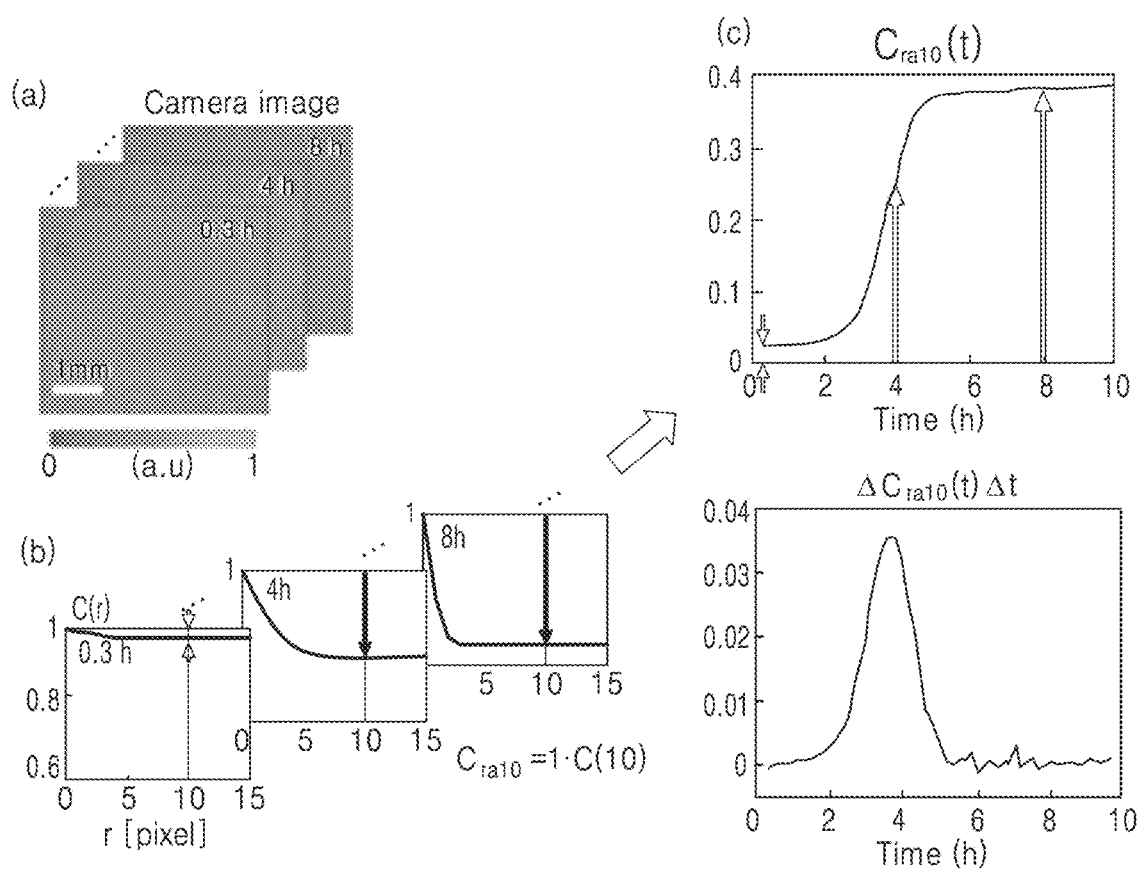

FIGS. 9 and 10 are diagrams for describing principles of detecting the microorganisms in a water examination device according to another embodiment of the present disclosure.

Referring to FIGS. 9 and 10, the controller 130 may receive optical images measured in a time-serial manner from the detector 120, and may determine the concentration information of microorganisms in a sample from the optical images.

The controller 130 may obtain a spatial correlation of an interference pattern. Here, the spatial correlation given by the equation below may represent, in a number within a certain range, how similar is between a brightness of a certain pixel and a brightness of another pixel away from the certain pixel by a distance r on an image measured at a time point t (see (b) of FIG. 10). The range may be between −1 and 1. That is, the spatial correlation indicates a degree of correlation between a certain pixel and another pixel, that is, 1 denotes a positive correlation, −1 denotes a negative correlation, and 0 denotes no correlation. In detail, because the brightness is uniform before the interference pattern is formed, the spatial correlation of a sample image denotes the positive correlation close to 1, but after the interference pattern is formed, the value of the correlation may be reduced toward 0.

The detector 120 defines a brightness measured at a time t from a pixel at a position r'=(x,y) as I(r',t) and defines a brightness of a pixel away from the above pixel by the distance r as I(r'+r, t). The spatial correlation may be expressed by Equation 5 below.

$$C(r, t) = \frac{1}{C_0(t)} \int \int I(r' + r, t) I(r', t) dr' \quad [\text{Equation 5}]$$

$C_0(t)$ was used to adjust the range of Equation 5 to −1 to 1. When a brightness I(r',t) of a certain pixel measured at a time t and a brightness I(r'+r,t) of a pixel away from the certain pixel by the distance r are equal to each other, the spatial correlation has a value of 1, and when the brightness is not identical, the spatial correlation has a value less than 1.

In an embodiment, the present disclosure may express the above spatial correlation only as a function of time. To do this, the controller 130 may obtain an average of the spatial correlation for a certain pixel and a pixel having the same size and away from by the distance r as in Equation 6 below (refer to (b) of FIG. 10).

$$C(\rho, t) = \frac{1}{2\pi} \int_0^{2\pi} C(r, t) d\theta \quad [\text{Equation 6}]$$

In an embodiment, the controller 130 may express the distance set in advance as a function of time by substituting the distance into Equation 6 above, and may identify a degree of forming the interference pattern as a value ranging from 0 to 1 (see (d) of FIG. 10).

The controller 130 may distinguish foreign substances from microorganisms in the sample through a change in the pattern of the sample image over time. In the case of foreign substances, there is no change in the image over time, but images such as shapes, sizes, etc. of the microorganisms are changed over time, and thus, the water examination device 100 may distinguish the foreign substances from the microorganisms.

In addition, the controller 130 may determine the concentration information of the microorganisms by using the spatial correlation as follows. The spatial correlation may be obtained by generating two identical images overlapping each other by using one image, shifting one of the two images by a preset distance in one direction, and analyzing how similar the two pixels are between the shifted image and the image that is not shifted. Here, the spatial correlation is a measure indicating how uniform an image is. When an interference pattern is formed due to a colony, similarity between two adjacent pixels decreases due to the small interference pattern, and a value of the spatial correlation also decreases.

The spatial correlation coefficient changes according to the shifted distance r (see (b) of FIG. 9), that is, the value of the spatial correlation coefficient decreases as the shifted distance r increases within a certain distance range and is nearly consistent when exceeding the certain distance range. Accordingly, in order to obtain a more meaningful spatial correlation, the controller 130 may obtain the spatial correlation by shifting the image by a certain distance set in advance or more. Here, the certain distance r set in advance depends on the speckle size, and the controller 130 may obtain the spatial correlation by shifting the image by a pixel that is greater than the speckle size when expressed in units of pixels. For example, the certain distance set in advance may be at least 3 pixels or more.

Meanwhile, the controller 130 may obtain a temporal correlation of the interference pattern of the measured sample image, as well as the spatial correlation as described above, and may detect the microorganisms based on the obtained temporal correlation. The controller 130 may calculate a temporal correlation coefficient between images by using image information of the interference pattern measured in a time-serial manner, and may detect a microorganism colony in the sample based on the temporal correlation coefficient.

The controller 130 may detect the microorganism through analysis about when the calculated temporal correlation coefficient falls below a reference value set in advance.

For the above analysis, the water examination device 100 according to the embodiment of the present disclosure may further include a multiple scattering amplification member for amplifying the number of times that the light incident into the cup 200 is multiple scattered in the sample. For example, a multiple scattering amplification member (not shown) is provided on a movement path of light between the wave source 110 and the cup 200 or between the cup 200 and the detector 120, and may amplify the number of times that the light is multiple scattered. The multiple scattering amplification member (not shown) may be installed on or detached from the water examination device 100, and may be used as necessary. Through the above-described configuration, the water examination device according to the embodiments of the present disclosure may detect the microorganisms in the fluid in the cup 200 within a short period of time.

While the present disclosure has been particularly shown and described with reference to preferred embodiments thereof, it will be understood by those skilled in the art that various changes in form and details may be made therein without departing from the spirit and scope of the present disclosure as defined by the appended claims. The preferred embodiments should be considered in descriptive sense only and not for purposes of limitation. Therefore, the scope of the present disclosure is defined not by the detailed description of the disclosure but by the appended claims, and all differences within the scope will be construed as being included in the present disclosure.

INDUSTRIAL APPLICABILITY

According to an embodiment of the present disclosure, there is provided a water examination device. Also, embodiments of the present disclosure may be applied to a device for measuring foreign substances in a fluid, etc.

The invention claimed is:
1. A water examination device comprising:
a main body;
a cup accommodation unit formed inward from a surface of the main body, and wherein the cup accommodation unit is adapted to receive a cup containing fluid;
a wave source for irradiating a wave toward the cup accommodation unit;
a detector for detecting a laser speckle generated by multiple scattering of the irradiated wave in the fluid, in time-serial manner; and a controller for estimating whether foreign substances exist in the fluid in real-time by using the detected laser speckle, wherein the cup accommodation unit comprises:

a bottom portion formed in the main body; and a wall portion extending from the bottom portion toward the surface of the main body, wherein the bottom portion and the wall portion form a receiving region that is adapted to receive the cup, and wherein the wall portion is formed to have an annular shape and is formed to be narrowed toward an upper portion of the main body; and wherein an angle between the bottom portion and the wall portion is not a right angle.

2. The water examination device of claim 1, wherein the angle ranges from 85° to 88°.

3. The water examination device of claim 1, wherein three or more support portions protrude from the bottom portion.

4. The water examination device of claim 3, wherein the bottom portion is substantially flat, and wherein the three or more support portions are adapted to contact the cup when the cup is received within the cup accommodation unit.

5. The water examination device of claim 1, wherein the bottom portion or the wall portion includes a multi-scattering amplification region for amplifying a number of times that the wave irradiated from the wave source is multiple scattered in the fluid.

6. The water examination device of claim 5, wherein the multi-scattering amplification region includes a multiple scattering material to amplifies the number of multiple scattering in the fluid by reflecting at least some of the wave emitted from the fluid onto the fluid.

7. The water examination device of claim 1, wherein the controller is configured to obtain a temporal correlation of the detected laser speckle by using the detected laser speckle, and estimate whether microorganisms exist in the fluid in real-time based on the obtained temporal correlation.

8. The water examination device of claim 7, wherein the temporal correlation includes a difference between first image information of the laser speckle detected at a first time point and second image information of the laser speckle detected at a second time point that is different from the first time point.

9. The water examination device of claim 8, wherein the first image information and the second image information include at least one of pattern information of the laser speckle and intensity information of the wave.

10. The water examination device of claim 1, wherein the controller is configured to obtain a spatial correlation of an interference pattern of an optical image detected by the detector, and determine whether microorganisms exist in the fluid based on a change in the spatial correlation of the interference pattern over time.

11. A water examination method comprising:

inserting, into a cup accommodation unit, a cup in which a fluid is capable of being accommodated;

irradiating, by a wave source, a wave having coherence to the cup accommodation unit, in which the cup is accommodated;

detecting, by a detector, a laser speckle generated by multiple scattering of the irradiated wave from the wave source in the fluid, in time-serial manner; and estimating, by a controller, whether microorganisms exist in the fluid in real-time by using the detected laser speckle, and wherein the cup accommodation unit comprises:

a bottom portion formed in the main body; and a wall portion extending from the bottom portion toward the surface of the main body and formed to surround at least a part of a side surface of a cup accommodated in the cup accommodation unit, wherein the wall portion is formed to have an annular shape and is formed to be narrowed toward an upper portion of the main body; and wherein an angle between the bottom portion and the wall portion is not a right angle.

* * * * *